United States Patent
Ansari et al.

(10) Patent No.: US 11,957,778 B2
(45) Date of Patent: *Apr. 16, 2024

(54) ORAL CARE COMPOSITIONS AND METHODS OF USE

(71) Applicant: Colgate-Palmolive Company, New York, NY (US)

(72) Inventors: Shamim Ansari, Princeton, NJ (US); Harsh Mahendra Trivedi, Hillsborough, NJ (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/406,069

(22) Filed: May 8, 2019

(65) Prior Publication Data

US 2019/0262254 A1    Aug. 29, 2019

Related U.S. Application Data

(63) Continuation of application No. 15/597,676, filed on May 17, 2017, now abandoned.

(51) Int. Cl.
| | |
|---|---|
| A61K 8/73 | (2006.01) |
| A61K 8/34 | (2006.01) |
| A61K 8/92 | (2006.01) |
| A61K 8/9794 | (2017.01) |
| A61Q 11/00 | (2006.01) |

(52) U.S. Cl.
CPC .............. *A61K 8/735* (2013.01); *A61K 8/345* (2013.01); *A61K 8/922* (2013.01); *A61K 8/9794* (2017.08); *A61Q 11/00* (2013.01)

(58) Field of Classification Search
CPC ......... A61K 31/047; A61K 35/50; A61K 8/73
USPC ............................................ 424/52, 57, 528
See application file for complete search history.

(56) References Cited

U.S. PATENT DOCUMENTS

| | | | | |
|---|---|---|---|---|
| 4,525,342 A * | 6/1985 | Weiss | | A61K 8/67 |
| | | | | 424/49 |
| 5,624,906 A * | 4/1997 | Vermeer | | A61K 8/60 |
| | | | | 514/23 |
| 6,350,435 B1 * | 2/2002 | Alvarez Hernandez | | |
| | | | | A61K 8/922 |
| | | | | 424/769 |
| 9,554,973 B2 | 1/2017 | O'Malley | | |
| 2002/0160077 A1 | 10/2002 | Gurin | | |
| 2006/0057175 A1 | 3/2006 | Ciccognani | | 424/405 |
| 2007/0207113 A1 | 9/2007 | Joerger | | A61Q 5/02 |
| | | | | 424/70.31 |
| 2008/0095719 A1 * | 4/2008 | Herrmann | | A61K 36/73 |
| | | | | 424/48 |
| 2008/0226756 A1 | 9/2008 | Willemin | | 424/732 |
| 2010/0022471 A1 | 1/2010 | Hanifl | | A61K 8/345 |
| | | | | 514/54 |
| 2013/0287708 A1 * | 10/2013 | Silberstein | | A61K 8/553 |
| | | | | 424/49 |
| 2014/0093582 A1 * | 4/2014 | Qian | | A61K 35/50 |
| | | | | 424/528 |
| 2014/0242005 A1 | 8/2014 | Koumans | | 424/57 |
| 2014/0349375 A1 | 11/2014 | Benjamin et al. | | |
| 2014/0356450 A1 | 12/2014 | Atomi | | 424/581 |
| 2015/0030546 A1 * | 1/2015 | O'Malley | | A61K 8/97 |
| | | | | 424/49 |
| 2016/0067167 A1 | 3/2016 | Prosise | | 424/50 |
| 2016/0166498 A1 * | 6/2016 | Anastassov | | A61K 8/19 |
| | | | | 424/52 |

FOREIGN PATENT DOCUMENTS

| | | | |
|---|---|---|---|
| KR | 11112498 | 10/2011 | |
| KR | 20110112498 | 10/2011 | .............. A61K 8/97 |
| RU | 2253436 | 6/2005 | |
| WO | 1998/003152 | 1/1998 | |
| WO | 2009/029434 | 3/2009 | |
| WO | WO 2014/049562 | 4/2014 | |
| WO | WO 2016/197015 | 12/2016 | |

OTHER PUBLICATIONS

Blagden: Specialty Chemicals, "Caprylyl Glycol." www.blagden.com/caprylyl-glycol. Jul. 16, 2019 (Year: 2019).*
Cannacosmetics (www.cannacosmetics.de), "Oral Health—Cosmetics with bio hemp seed oil." Published online Mar. 1, 2016. ( Year: 2016).*
Cannacosmetics, "Annabis Orcann Mundwasser mit Hanfol." https://www.cannacosmetics.de/: published online wayback date Apr. 18, 2016. (Year: 2016).*
International Search Report and Written Opinion of the International Searching Authority in International Application No. PCT/US2017/033087, dated Jan. 8, 2018.
Wan Budnikowsky, 2016, "Mouthwash Fresh," Mintel GNPD AN: 3939211.
Kukina, 2005, "Agent for treating oral cavity mucosa diseases and inflammatory diseases of periodontal tissues," WP Thomson Database AN 2005-539574.
Varvaresou at al., "Self-preserving cosmetics," International Journal of Cosmetic Science, 2009, 31 163-175.
Wallace, Terry, "Hemp Seed Oil Pulling for Healing Originating From Ayurvedic Medicine," Agency Inc.; www.hempout.com; 2 pages; posted on Apr. 2, 2014.
Yardley et al., 2016, "Haptic characterization of human skin in vivo in response to shower gels using a magnetic leviation device," Skin Research and Technology 22(1):115-127.

(Continued)

*Primary Examiner* — Walter E Webb

(57) ABSTRACT

Disclosed herein are oral care compositions comprising hemp seed oil and caprylyl glycol. In certain embodiments, the oral care composition optionally further comprises one or more ingredients selected from hyaluronic acid and aloe vera. Methods of making and using the compositions are also provided.

18 Claims, No Drawings

(56) References Cited

OTHER PUBLICATIONS

Apidos, Rachel, "Hemp Seed Oil vs. CBD Oil: Two Totally Different Things-Here's What Tto Know," Wellgood, Feb. 12, 2019 (date obtained Mar. 9, 2020) <https://www.wellandgood.com/good-looks/hemp-oil-vs-cbd-oil/>.

Leizer, et al., "The Composition of Hemp Seed Oil and Its Potential as an Important Source of Nutrition," Journal of Nutraceuticals, Functional & Medical Foods. 2(4):35-53. (2000).

Murray, Dana, "CBD Oil vs. Hempseed Oil: How to Know What You're Paying For," Healthline, Dec. 23, 2019 (date obtained Mar. 9, 2020) <https://www.healthline.com/health/hemp-vs-cbd-oil#1>.

Wilson, Debra Rose, "Hemp oil benefits list," Medical News Today, Feb. 14, 2019 (date obtained Mar. 9, 2020) <https://www.medicalnewstoday.com/articles/324450>.

Toliver, et al., "Caprylyl Glycol: A Versatile Material to Boost Preservatives," Cosmetics & Toiletries, pp. 1-3.

Jeong, "Tooth paste composition containing hemp seed oil," (2011).

Jeong, "Tooth paste composition containing hemp seed oil," English translation <https://patents.google.com/patent/KR20110112498A/en?oq=KR2011-0112498+>.

"Tooth composition containing hemp seed oil," Certified English translation (2011).

Annabis Hemp Cosmetics, "Annabis Orcann Natural Concentrated Mouthwash," www.annabishemp.com/product/annabis-orcann-natural-concentrated-mouthwash/ (last accessed Dec. 5, 2022).

Annabis North America, "Annabis ORCANN All-Natural Concentrated Hemp Mouthwash—1.01 fl oz," www.annabis.us/shop/product/annabis-orcann-all-natural-hemp-concentrated-mouthwash/ (last accessed Dec. 5, 2022).

CBD Solution di Caprio Franicesco, "Orcann Concentrated Cosmetic Mouthwash 30 ml Annabis," www.shop-cannabislight.com/en/cosmetics/34-orcann-concentrated-cosmetic-mouthwash-30ml-annabis.html (last accessed Dec. 5, 2022).

Hempshopper, "Annabis Medical Orcann Mouthwash 30 ml," hempshopper.com/product/hemp-body-care/annabis-medical-orcann-mouthwash-30ml/ (last accessed Dec. 5, 2022).

Simply Green B.V., "Wholesale Annabis Orcann Hemp Mouthwash Dilutable Drops," www.simplygreentrade.com/product/annabis-orcann-hemp-mouthwash-dilutable-drops-30ml (last accessed Dec. 5, 2022).

* cited by examiner

ORAL CARE COMPOSITIONS AND METHODS OF USE

FIELD

This invention relates to oral care compositions comprising hemp seed oil and caprylyl glycol. In certain embodiments, the oral care composition optionally further comprises one or more ingredients selected from hyaluronic acid and aloe vera. The invention also describes methods of making and using these compositions.

BACKGROUND

Dry mouth, or xerostomia, is a subjective complaint of one's mouth feeling dry. It is usually caused by a reduction in salivary flow or by changes in the biochemical composition of saliva. Dryness of mouth is a major cause of oral stress and discomfort experienced by many individuals. Epidemiologically, dryness of the mouth is one of the most prevalent oral discomforts experienced by millions of people in the United States and around the globe. In one estimate, 44 million people in the United States alone are affected by xerostomia. Although dry mouth symptoms can affect persons of any age group, dry mouth is more likely to occur in middle and older age groups. Further, an increased prevalence of dry mouth among older age groups may not be due to aging, but instead may be due to underlying disease conditions, such as Sjögren's Syndrome, diabetes, cancer and stroke. In general, many cases of dry mouth are linked to the use of prescription drugs or over-the-counter medications. There are more than 1800 drugs which have the capacity to induce xerostomia, hence those drugs are termed as "xerogenic".

Dry mouth can lead to a parched feeling in the throat, stickiness and cotton-ness in the mouth which can make it challenging to eat, drink, or even talk. Dry mouth can also make the throat feel sore and scratchy because of lack of enough lubricant from saliva. A persistent dry mouth condition could impair taste receptors, increase the risk of developing dental cavities, or increase occurrence of bacterial and fungal infections.

International patent application publication No. WO2014/049562 discloses an oral cosmetic having a combination of active agents comprising at least one polyunsaturated fatty acid and at least one carotenoid, for improving the quality of the nails. In certain embodiments, the at least one polyunsaturated fatty acid may be hemp oil.

U.S. patent application publication No. US2014/0349375 discloses the use of methylsulfonylmethane (MSM) to modulate microbial activity. In certain embodiments, the MSM may be combined with hemp seed oil. In certain embodiments, the MSM may be added to oral care products, such as toothpaste, mouthwash, or mouth-irrigant.

South Korean patent application No. KR2011-0112498 discloses a toothpaste composition containing 0.1-4.0 weight % of Cannabis sativa L. seed oil.

International patent application publication No. WO2016/197015 discloses a composition and method for whitening and restoring natural tooth color, and a composition for application to a skin cell, or a portion of an area of skin. In certain embodiments, the composition comprises hemp oil. In certain embodiments, the inventors contemplate application of the composition as a mouthwash.

Current oral care market products do not adequately address oral dryness and discomfort. Accordingly, there is a need for oral compositions to provide effective relief by ameliorating and/or preventing dry mouth discomfort.

SUMMARY OF THE INVENTION

It has been surprisingly found that oral care compositions comprising hemp seed oil and caprylyl glycol show unexpected benefits within oral models. In certain embodiments, such compositions may optionally contain one or more molecules selected from hyaluronic acid and aloe vera.

In one embodiment, the invention is an oral care composition comprising hemp seed oil and caprylyl glycol. In certain embodiments, the hemp seed oil is present at a concentration from 0.8 to 1.2%, by weight of the composition. In certain embodiments, the hemp seed oil is present at a concentration of 1.0%, by weight of the composition. In certain embodiments, the hemp seed oil is present at a concentration from 0.8 to 1.2%, by weight of the composition and caprylyl glycol is present at a concentration of 0.15 to 0.35%, by weight of the composition. In certain embodiments, the hemp seed oil is present at a concentration from 0.8 to 1.2%, by weight of the composition and caprylyl glycol is present at a concentration of 0.25%, by weight of the composition.

In further embodiments, the invention is an oral care composition comprising hemp seed oil and caprylyl glycol, further comprising aloe vera. In certain embodiments, the aloe vera is present at a concentration of 0.15 to 0.35%, by weight of the composition. In certain embodiments, the aloe vera is present at a concentration of 0.25%, by weight of the composition.

In further embodiments, the invention is an oral care composition comprising hemp seed oil and caprylyl glycol, further comprising hyaluronic acid. In certain embodiments, the hyaluronic acid is present at a concentration of 0.01 to 0.1%, by weight of the composition. In certain embodiments, the hyaluronic acid is present at a concentration of 0.05%, by weight of the composition.

In further embodiments, the invention is a method to improve oral health comprising applying an effective amount of any of the oral compositions described above to the oral cavity of a subject in need thereof. In certain embodiments, the improved oral health may be selected from one or more of the following; a. reduce or inhibit formation of dental caries; b. reduce, repair or inhibit early enamel lesions; c. reduce or inhibit demineralization and promote remineralization of the teeth; d. reduce hypersensitivity of the teeth; e. reduce or inhibit gingivitis; f. promote healing of sores or cuts in the mouth; g. reduce levels of acid producing bacteria; h. to increase relative levels of arginolytic bacteria; i. inhibit microbial biofilm formation in the oral cavity; j. raise and/or maintain plaque pH at levels of at least pH 5.5 following sugar challenge; k. reduce plaque accumulation; l. treat, relieve or reduce dry mouth; m. whiten teeth; n. enhance systemic health, including cardiovascular health; o. reduce erosion of the teeth; p. immunize the teeth against cariogenic bacteria and their effects; q. clean the teeth and oral cavity; r. reduce inflammation; s. increase anti-oxidant levels; t. reduce oral discomfort; u. increase lubrication; v. reduce tissue friction due to drying; and w. increase tissue hydration.

In certain embodiments, the invention is a composition obtained or obtainable by combining the ingredients as set forth in any of the preceding compositions and methods.

DETAILED DESCRIPTION

The following description of embodiment(s) of the invention is merely exemplary in nature and is in no way intended to limit the invention, its application, or uses.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used throughout, ranges are used as shorthand for describing each and every value that is within the range. Any value within the range can be selected as the terminus of the range.

Unless stated otherwise, all percentages of composition components given in this specification are by weight based on a total composition or formulation weight of 100%. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art.

All references cited herein are hereby incorporated by reference in their entireties. In the event of a conflict in a definition in the present disclosure and that of a cited reference, the present disclosure controls.

As used herein, the term "oral composition" means the total composition that is delivered to the oral surfaces. The composition is further defined as a product which, during the normal course of usage, is not for the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, dental strips, beads, lozenge, varnish, paint-on composition, toothpowder, chewing gum and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

The term "mouth rinse" in the present invention refers to oral compositions that are substantially liquid in character, such as a mouth wash, spray, rinses, and the like. In such a preparation the orally acceptable carrier typically has an aqueous phase comprising water or a water and alcohol mixture. Further, in various embodiments, the oral carrier includes a humectant and surfactant. Generally, if alcohol is present, the weight ratio of water to alcohol is in the range of 1:1 to 20:1, preferably 3:1 to 10:1 and more preferably 4:1 to 6:1. The total amount of water-alcohol mixture in this type of preparation is typically in an amount of 70 to 99.9% of the preparation. In various embodiments, the alcohol is typically ethanol or isopropanol.

The compositions of the invention may be applied to the oral cavity of a subject (in particular to the oral cavity of a human or animal subject) by any means. The application means may vary depending on the formulation of the oral care composition. For example, in certain embodiments the oral care composition is a dentifrice and may be applied to the oral cavity topically using an implement (such as a brush, toothbrush, stick, sponge or cotton swab). In certain embodiments, the oral care composition is in the form of a mouthwash or mouth rinse and is applied to the oral cavity by lavage ("swish"). In certain embodiments, the mouthwash or mouth rinse is in a single phase. In certain embodiments, the mouthwash or mouth rinse is in a dual phase. In certain embodiments the oral care composition is applied to surfaces in the oral cavity using a dental tray. In certain embodiments the oral care composition is applied to surfaces in the oral cavity using a dental strip, for example by affixing a strip comprising the oral care composition to the surface of the teeth or gums. In certain embodiments the oral care composition is administered to the oral cavity using an oral care pen. In certain embodiments the oral care composition is applied to the oral cavity at least once or at least twice per day.

The term "effective amount" as used herein means that the amount of the composition of the present invention is of sufficient quantity to achieve the intended purpose, such as, for example, to ameliorate and/or prevent dry mouth discomfort in the subject.

The term "hemp seed oil" as used herein means an oil composition derived from hemp seeds. In contrast, "hemp oil" is made of one or more materials selected from the leaves, flowers and the fibre of hemp plants.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes, for example, excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

The invention provides for oral care compositions comprising hemp seed oil. In certain embodiments, the oral care composition may optionally further comprise one or more ingredients selected from caprylyl glycol, hyaluronic acid and aloe vera. In some embodiments, the oral care composition contains hemp seed oil at 0.6 to 1.4% by weight. In certain embodiments, the hemp seed oil is 0.8 to 1.2% by weight of the oral care composition. In further embodiments, hemp seed oil is 1.0% by weight of the oral care composition.

In further embodiments, the invention provides for oral care compositions comprising hemp seed oil and caprylyl glycol. In certain embodiments, the oral care composition may optionally further comprise one or more ingredients selected from hyaluronic acid and aloe vera. Such compositions provide unique features, such as oral comfort benefits. In some embodiments, the hemp seed oil is present at 0.6 to 1.4% by weight of the composition. In certain embodiments, the hemp seed oil is present at 0.8 to 1.2% by weight of the oral care composition. In further embodiments, the hemp seed oil is present at 1.0% by weight of the oral care composition. In certain embodiments, the caprylyl glycol is present at a concentration of 0.15 to 0.35%, by weight of the composition. In further embodiments, the caprylyl glycol is present at a concentration of 0.25%, by weight of the composition. In some embodiments, the hemp seed oil is present at 0.6 to 1.4% and caprylyl glycol is present at 0.15 to 0.35%, by weight of the composition. In certain embodiments, the hemp seed oil is present at 0.8 to 1.2% and caprylyl glycol is present at 0.2 to 0.3%, by weight of the oral care composition. In further embodiments, the hemp seed oil is present at 1.0% and caprylyl glycol is present at 0.2 to 0.3%, by weight of the oral care composition. In further embodiments, the hemp seed oil is present at 1.0% and the caprylyl glycol is present at a concentration of 0.25%, by weight of the composition.

In some embodiments, the oral care composition contains hemp seed oil, caprylyl glycol and aloe vera. In some embodiments, the hemp seed oil is present at 0.6 to 1.4%, caprylyl glycol is present at 0.15 to 0.35% and aloe vera is present at 0.15 to 0.35%, by weight of the composition. In certain embodiments, the hemp seed oil is present at 0.8 to 1.2%, caprylyl glycol is present at 0.2 to 0.3% and aloe vera is present at 0.2 to 0.3%, by weight of the oral care composition. In further embodiments, the hemp seed oil is present at 1.0%, caprylyl glycol is present at 0.2 to 0.3% and aloe vera is present at 0.2 to 0.3%, by weight of the oral care composition. In certain embodiments, the hemp seed oil is present at 1.0%, caprylyl glycol is present at a concentration of 0.25% and aloe vera is present at 0.2 to 0.3%, by weight of the composition. In further embodiments, the hemp seed oil is present at 1.0%, caprylyl glycol is present at a concentration of 0.25% and aloe vera is present at 0.25"%, by weight of the composition.

In some embodiments, the oral care composition contains hemp seed oil, caprylyl glycol and hyaluronic acid. In some embodiments, the hemp seed oil is present at 0.6 to 1.4%, caprylyl glycol is present at 0.15 to 0.35% and hyaluronic acid is present at 0.01 to 0.1%, by weight of the composition. In certain embodiments, the hemp seed oil is present at 0.8 to 1.2%, caprylyl glycol is present at 0.2 to 0.3% and hyaluronic acid is present at 0.01 to 0.1%, by weight of the oral care composition. In further embodiments, the hemp seed oil is present at 1%, caprylyl glycol is present at 0.2 to 0.3%, and hyaluronic acid is present at 0.01 to 0.1%, by weight of the composition. In further embodiments, the hemp seed oil is present at 1.0%, caprylyl glycol is present at a concentration of 0.25% and hyaluronic acid is present at 0.05'%, by weight of the composition.

The invention further provides a method to improve oral health comprising applying an effective amount of an oral care composition described herein to a subject in need thereof. In certain embodiments, the oral health may be to reduce or inhibit formation of dental caries; reduce, repair or inhibit early enamel lesions; reduce or inhibit demineralization and promote remineralization of the teeth; reduce hypersensitivity of the teeth; reduce or inhibit gingivitis; promote healing of sores or cuts in the mouth; reduce levels of acid producing bacteria; to increase relative levels of arginolytic bacteria; inhibit microbial biofilm formation in the oral cavity; raise and/or maintain plaque pH at levels of at least pH 5.5 following sugar challenge; reduce plaque accumulation; treat, relieve or reduce dry mouth; whiten teeth; enhance systemic health, including cardiovascular health; reduce erosion of the teeth; immunize the teeth against cariogenic bacteria and their effects; clean the teeth and oral cavity; reduce inflammation; increase anti-oxidant levels; reduce oral discomfort; increase lubrication; reduce tissue friction due to drying; and increase tissue hydration.

In certain embodiments, the hemp seed oil, caprylyl glycol and optionally one or more ingredients selected from hyaluronic acid and aloe vera are included in oral care compositions. In some embodiments, the oral care composition may be selected from the group selected from a toothpaste or a dentifrice, a mouth rinse, a topical oral gel, a denture cleanser, dental strips, beads, lozenge, varnish, and a paint-on composition. In some embodiments, the oral care composition may be toothpaste or a dentifrice. In some embodiments, the oral care composition may be a mouth rinse. In some embodiments, the oral care composition may be a topical oral gel and a denture cleanser.

In further embodiments, the invention is a method to improve oral health comprising applying an effective amount of an oral composition described herein to the oral cavity of a subject in need thereof. In certain embodiments, the method includes use of hemp seed oil, caprylyl glycol and optionally one or more ingredients selected from hyaluronic acid and aloe vera. In certain embodiments, the method includes an oral care composition which is selected from the group consisting of a toothpaste or a dentifrice, a mouthwash or a mouth rinse, a topical oral gel, a denture cleanser, dental strips, beads, lozenge, varnish, paint-on composition, toothpowder and the like.

The invention further provides methods to ameliorate and/or prevent dry mouth discomfort, reduce oral discomfort, increase lubrication, reduce tissue friction due to drying, and increase tissue hydration, comprising applying an effective amount of a composition of the invention, e.g., any of said compositions described herein, to the oral cavity.

For example, the invention provides methods to ameliorate and/or prevent dry mouth discomfort, reduce and inhibit acid erosion of the enamel, reducing or inhibiting gum recession, controlling microbial growth, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of said compositions described herein, to the oral cavity, and then rinsing with sufficient water or aqueous solution.

Some embodiments provide a mouthwash for use in ameliorating and/or preventing dry mouth discomfort, reducing or inhibiting acid erosion of the enamel, reducing or inhibiting gum recession, controlling microbial growth, cleaning the teeth, reducing bacterially-generated biofilm and plaque, reducing gingivitis, inhibiting tooth decay and formation of cavities, and/or reducing dentinal hypersensitivity.

Some embodiments provide the use of hemp seed oil, caprylyl glycol and optionally one or more ingredients selected from hyaluronic acid and aloe vera to be included in oral care compositions for the manufacture of a mouthwash. Other embodiments provide a method of treating or reducing dental enamel erosion, cleaning the teeth, reducing or inhibiting gum recession, reducing bacterially-generated biofilm and plaque, reducing gingivitis, inhibiting tooth decay and formation of cavities, and/or reducing dentinal hypersensitivity comprising applying a mouthwash as described herein. Other embodiments provide methods further comprising the step of rinsing with sufficient water or aqueous solution.

The invention further provides a method of making an oral care composition comprising combining hemp seed oil, caprylyl glycol and optionally one or more ingredients selected from hyaluronic acid and aloe vera in an aqueous medium solution with other oral care ingredients known to one of skill in the art. In certain embodiments, the oral care composition is a toothpaste. In certain embodiments, the oral care is a mouthwash base.

"Actives," means compounds that, when applied to a target tissue, provide a benefit or improvement to the target tissue. The actives can be delivered in the form of any oral care formulations, for example a toothpaste, transparent paste, gel, mouthwash, powder, cream, strip, spray, gum, or any other known in the art.

If the ingredients are delivered in the form of a mouthwash, a person desiring the benefits rinses with the solution containing the ingredients of the invention. In certain embodiments, a dual chamber may be implemented. In such aspects, a first chamber contains one or more of the ingredients of the invention. The dual chamber will also contain a second chamber containing solubilized one or more further ingredients of the invention. Upon application, the contents of the first and second chamber are mixed together, thus producing the complete solution comprising each ingredient of the invention.

In another embodiment, the mixture is prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel. In certain embodiments, the complex is formulated in a composition comprising Carbopol® polymer, glycerin and water.

In another embodiment, the stock solution, or a mixture of stock solution with water, is applied to the teeth in a gel formulation, e.g., wherein the gel can stay on the tooth for an extended period of time for effective treatment.

In another embodiment, the composition of the present invention is a viscous liquid, preferably a gel, which maintains its consistency during storage enabling the product to be painted on the tooth surface with a soft applicator pen or brush. Some embodiments provide a method utilizing an applicator to deliver the composition, wherein the applicator is a pen and the pen is stored within an oral care implement. In some embodiments, the pen is removed from the oral care implement prior to application of the composition to the tooth. In some embodiments, the composition is applied to the tooth after brushing. In some embodiments, the composition is applied to the tooth after brushing with the oral care implement.

In certain embodiments, the composition is anhydrous. By anhydrous, there is less than 5% by weight water, optionally less than 4, less than 3, less than 2, less than 1, less than 0.5, less than 0.1 down to 0% by weight water.

A dentifrice or paste for localized application to a sensitive tooth site such as breeched cementum of an orally exposed root surface may be one that is simpler in composition and applied with a soft applicator. Such a dentifrice or paste may or may not contain conventional abrasive, foaming agent, and flavoring agents. Localized sites such as the dentine following tooth preparation for a dental restoration also involve simpler compositions and include fillers used in dental pulp cappings, cavity liners and cements and any other ingredients required for the composition by those skilled in the art (Craig et al., 1989, Restorative Dental Materials. Mosby, St. Louis, pp. 189-225). For example, zinc oxide and eugenol at levels of (20 and 25%, respectively) would be appropriate for dental cement compositions.

In certain embodiments, oral care compositions having ingredients of the invention further comprise one or more agents selected from diluents, bicarbonate salts, pH modifying agents, surfactants, foam modulators, additional thickening agents, humectants, sweeteners, flavorants, pigments, antibacterial agents, anticaries agents, fluoride ion sources, antioxidants, anti-hypersensitivity agents, anti-calculus or tartar control agents, and mixtures thereof.

The oral composition according to the present invention may optionally include other materials, such as for example, cleaning agents, flavouring agents, sweetening agents, adhesion agents, surfactants, foam modulators, abrasives, pH modifying agents, humectants, moisturizers, mouth feel agents, colorants, abrasives, preservatives, fluoride ion source, saliva stimulating agents, emollients, viscosity modifiers, diluents, emulsifiers, nutrients and combinations thereof. Various components that may be added to the oral composition include, for example, a sweetening agent such as saccharin, or sodium saccharin, alcohols such as ethanol, fluoride ion sources such as sodium fluoride, as well as glycerine, sorbitol, polyethylene glycols. Poloxamer polymers such as POLOXOMER® 407, PLURONIC® F108, (both available from BASF Corporation), alkyl polyglycoside (APG), polysorbate, PEG40, castor oil, menthol, and the like. It is understood that while general attributes of each of the above categories of materials may differ, there may be some common attributes and any given material may serve multiple purposes within two or more of such categories of materials. Preferably, such carrier materials are selected for compatibility with the active ingredients, as well as with other ingredients of the composition.

Some embodiments further comprise an effective amount of a fluoride ion source within the composition.

In other embodiments, the invention comprises an orally acceptable base comprising ingredients selected from one or more of buffering agents, humectants, surfactants, thickeners, breath fresheners, flavoring, fragrance, coloring, antibacterial agents, whitening agents, agents that interfere with or prevent bacterial attachment, calcium sources, phosphate sources, orally acceptable potassium salts, and anionic polymers.

Compositions of the inventions optionally contain other ingredients such as enzymes, vitamins and anti-adhesion agents. Enzymes such as proteases can be added for anti-stain and other effects. Non-limiting examples of vitamins include vitamin C, vitamin E, vitamin B5, and folic acid. In various embodiments, the vitamins have antioxidant properties. Anti-adhesion agents include ethyl lauroyl arginine (ELAH), solbrol, ficin, silicone polymers and derivatives, and quorum sensing inhibitors.

Flavorants among those useful herein include any material or mixture of materials operable to enhance the taste of the composition. Any orally acceptable natural or synthetic flavorant can be used, such as essential oils, various flavoring aldehydes, flavoring oils, esters, alcohols, similar materials, as well as sweeteners such as sodium saccharin, and combinations thereof. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. Flavorants include vanillin, sage, marjoram, parsley oil, spearmint oil, cinnamon oil, oil of wintergreen (methylsalicylate) peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methane glycerol acetal (MGA) and mixtures thereof. One or more flavorants are optionally present in a total amount of 0.01% to 5%, optionally in various embodiments from 0.05 to 2%, from 0.1% to 2.5%, and from 0.1 to 1.0%.

Sweetening agents among those useful herein include dextrose, polydextrose, sucrose, maltose, dextrin, dried invert sugar, mannose, xylose, ribose, fructose, levulose galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition of the invention.

The composition may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of 0.001% to 20%, for example 0.01% to 10% or 0.1% to 5%.

Active Agents:

The compositions of the invention may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste, for example, will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 weight % (expressed as weight of free base), e.g., about 1 to about 10 weight % for a consumer toothpaste or about 7 to about 20 weight % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product.

The compositions of the preferred embodiments also may optionally contain one or more antibacterial agents. The antibacterial agent may be selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, zinc oxide, stannous salts, copper salts, iron salts), sanguinarine propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing. In some embodiments, the antibacterial agent preferably is not triclosan, and may be selected from CPC, chlorhexidine, zinc citrate, zinc oxide, and mixtures thereof. If used, the antibacterial agent preferably is present in an amount of from 0.01% to 10%, for example from 0.025% to 5% by weight, more preferably from 0.05% to 1%, or from 0.075% to 0.5% by weight, based on the total weight of the composition. Levels of antibacterial agents may vary depending on the oral composition, with levels used in toothpaste being e.g., about 5 to about 15 times greater than used in mouth rinse. For example, a triclosan toothpaste may contain about 0.3 weight % triclosan.

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride (such as, but not limited to, olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 100 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 weight % to about 10 weight % in one embodiment or about 0.03 weight % to about 5 weight %, and in another embodiment about 0.1 weight % to about 1 weight % by weight of the composition in another embodiment. Weights of fluoride salts to provide the appropriate level of fluoride ion will obviously vary based on the weight of the counterion in the salt.

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, P1-6 phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP) ($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

The composition of the present invention may optionally incorporate one or more antisensitivity agents, e.g., potassium salts such as potassium nitrate, potassium bicarbonate, potassium chloride, potassium citrate, and potassium oxalate; capsaicin; eugenol; strontium salts; and combinations thereof. Such agents may be added in effective amounts, e.g., from about 1 wt. % to about 20 wt. % by weight based on the total weight of the composition, depending on the agent chosen.

The oral care compositions of the invention may also include additional polymers to adjust the viscosity of the formulation or enhance the solubility of other ingredients. Such additional polymers include polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

The oral compositions may comprise significant levels of water. Water employed in the preparation of commercial oral compositions should be deionized and free of organic impurities. The amount of water in the compositions includes the free water which is added plus that amount which is introduced with other materials.

Within certain embodiments of the oral compositions, it is also desirable to incorporate a humectant to reduce evaporation and also contribute towards preservation by lowering water activity. Certain humectants can also impart desirable sweetness or flavor to the compositions. The humectant may be present in the composition in an amount of from 10 weight % to 40 weight % in one embodiment, or from 15 weight % to 30 weight % in another embodiment, by total weight of the composition. Suitable humectants include edible polyhydric alcohols such as glycerine, sorbitol, xylitol, propylene glycol as well as other polyols and mixtures of these. Typically, the composition of the present invention comprises a combination of glycerine and sorbitol.

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine. In certain embodiments, the basic amino acid is arginine, for example, L-arginine, or a salt thereof.

In certain embodiments, the basic amino acid is present in an amount corresponding to 0.1% to 15%, e.g., 0.1 weight % to 10 weight %, e.g., 0.1 to 5 wt %, e.g., 0.5 weight % to 3 weight % of the total composition weight, about e.g., 1%, 1.5%, 2%, 3%, 4%, 5%, or 8%, wherein the weight of the basic amino acid is calculated as free form.

In certain embodiments, salts are used within the formulation. Suitable salts include salts known in the art to be pharmaceutically acceptable salts and are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

The invention may, in some embodiments, contain anionic surfactants, for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 10%, in another embodiment 0.3% to 7% and in another embodiment 0.5% to 2% by weight of the total composition.

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of 0.01 to 1.5% by weight of the composition.

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 weight % pyrophosphate ions, e.g., 0.1 to 3 wt 5, e.g., 0.1 to 2 weight %, e.g., 0.1 to 1 wt %, e.g., 0.2 to 0.5 wt %. The pyrophosphates also contribute to preservation of the compositions by lowering water activity.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Silica may also be available as a thickening agent, e.g., synthetic amorphous silica. Colloidal magnesium aluminum silicate or finely divided silica can be used as component of the thickening composition to further improve the composition's texture. In certain embodiments, thickening agents in an amount of about 0.5% to about 5.0% by weight of the total composition are used. Thickeners may be present in an amount of from 1 weight % to 15 weight %, from 3 weight % to 10 weight %, 4 weight % to 9 weight %, from 5 weight % to 8 weight %, for example 5 weight %, 6 weight %, 7 weight %, or 8 weight %.

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example, a small particle silica may have an average particle size (D50) of 2.5-4.5 microns. Simply because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof.

In certain embodiments, any silica suitable for oral care compositions may be used, such as precipitated silicas or silica gels. For example, the silica can also be small particle silica (e.g., Sorbosil AC43 from PQ, Warrington, United Kingdom). The composition preferable contains from 5 to 20 weight % small particle silica, or for example 10-15 weight %, or for example 5 weight %, 10 wt %, 15 weight % or 20 weight % small particle silica.

In another embodiment, the abrasive may be high cleaning precipitated silica having a pellicle cleaning ratio (PCR) of greater than 85 when tested at 20% loading is known in the art as high cleaning silica. Typically, high cleaning silica also has a mean particle size $d_{50}$ of from 5 to 15 μm and an oil absorption of from 40 to 120 $cm^3/100$ g silica. The cleaning efficacy of the precipitated silica is expressed using the pellicle cleaning ratio (PCR). This is typically measured at 20% silica loading. The high cleaning silica preferably has a PCR value of greater than 85. The efficacy of the precipitated silica can also be expressed with reference to its abrasive characteristic using the radioactive dentin abrasion (RDA). Ideally, RDA values for an oral composition should be below about 250 to protect tooth enamel/dentin. Methods of performing PCR and RDA are described in e.g., U.S. Pat. Nos. 5,939,051 and 6,290,933 and "In Vitro Removal of Stain With Dentifrice", G. K. Stookey et al., *J. Dental Research*, Vol. 61, pages 1236-9, November 1982. Typically, the precipitated silica has a mean particle size $d_{50}$ of from 5 to 15 μm and an oil absorption of from 40 to 120 $cm^3/100$ g silica. Examples of precipitated silica having a mean particle size $d_{50}$ of from 5 to 15 μm and an oil absorption of from 40 to 120 $cm^3/100$ g silica including commercially available silicas such as Zeodent® 103 and Zeodent® 105 (Huber Silica Americas).

The composition preferable contains from 3 to 20 weight % high cleaning precipitated silica, or for example 10-15 weight %, or for example 5 weight %, 10 wt %, 15 weight % or 20 weight % high cleaning precipitated silica.

The composition may also comprise an abrasive silica having an acid pH in the composition. For example, prophy silica available from Grace, offered as Sylodent™, can be used. The acidic silica abrasive is included in the dentifrice components at a concentration of about 2 to about 35% by weight; about 3 to about 20% by weight, about 3 to about 15% by weight, about 10 to about 15% by weight. In certain embodiments, the acidic silica abrasive may be present in an amount between 2-7%. In other embodiments, it may be present in an amount between 7-15% by weight. Still on other embodiments, it may be present in an amount between 15-30% by weight. For example, the acidic silica abrasive may be present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %.

A commercially available acidic silica abrasive is Sylodent 783 available from W. R. Grace & Company (Baltimore, Md.). Sylodent 783 has a pH of 3.4-4.2 when measured as a 5% by weight slurry in water. For use in the present invention, the silica material has an average particle size of less than 10 microns, e.g., 3-7 microns, e.g. about 5.5 microns.

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, dipotassium phosphate, tribasic sodium phosphate, sodium tripolyphosphate, phosphoric acid), citrates (e.g. citric acid, trisodium citrate dehydrate), pyrophosphates (sodium and potassium salts) and combinations thereof. The amount of buffering agent is sufficient to provide a pH of about 5 to about 9, preferable about 6 to about 8, and more preferable about 7, when the composition is dissolved in water, a mouth rinse base, or a toothpaste base. Typical amounts of buffering agent are about 5% to about 35%, in one embodiment about 10% to about 30%, in another embodiment about 15% to about 25%, by weight of the total composition.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

The present invention in its method aspect involves applying to the oral cavity a safe and effective amount of the compositions described herein.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Measurement of Frictional Coefficient

The apparatus used in these studies uses a modification of a butterfly haptics Magnetic Levitation Haptic Device (MLHD) manufactured by Butterfly Haptics (Pittsburgh, PA) and a custom tactor (see Yardley et al., Skin Research and Technology, 2016; 22: 115-127). The MLHD is a six degree-of-freedom (6-DOF) device which uses six Lorentz actuator coils to produce rotational and linear forces on a central component known as the 'flotor'. While in operation, the flotor of the MLHD has no physical contact with the rest of the device, and as a result there is no friction or backlash produced. The MLHD is capable of moving the flotor in a 24 mm spherical diameter with a position resolution of <2.0 microns and a position bandwidth of 140 Hz. The MLHD is also capable of producing a maximum force of 40 N at a bandwidth of >2000 Hz with a resolution of 20 mN.

Since the MLHD does not come equipped with a force/torque sensor, the flotor of the MLHD was modified to accept an ATI Nano-17 6-axis force/torque sensor (ATI Industrial Automation, Apex, NC). The sensor was fastened between two aluminum plates of area 968 mm$^2$ with the tactor bolted to both aluminum plates and a brass coupler secured to the bottom plate.

In order to test in vitro porcine tongues with the MLHD, a platform was constructed to hold the tongue sample and allow the tactor to make contact with it. The platform was custom made from a 762 mm×203 mm×3.2 mm aluminum plate with a 38.1 mm×19 mm slot milled in the center to expose a section of the tongue sample to be tested. The dimensions of the slot were experimentally determined. The platform was secured to a pair of laboratory jacks by fitting two screws into each jack. The screws were placed through a pair of corresponding holes located at each end of the platform and the position of the jacks was maintained by using masking tape to mark two square areas on the desk housing the MLHD. A platform height of 114 mm was used.

Once a tongue sample was secured to the platform, the control algorithm was activated and the tactor moved across the surface of the tongue sample. The tactor moved a length of 22 mm ten times while maintaining a constant normal force of 0.1 N and a velocity of 1 mm/second. Since the length of the MLHD workspace is 24 mm along the x-axis, the 22 mm stroking distance allows a maximum amount of data to be collected while maintaining a safe distance from the edge of the workspace.

Porcine tongue closely approximates human tongue. Each has anterior sections which are covered by fungiform papillae scattered between filiform papillae. Fungiform papillae are mushroom shaped and contain taste buds. Filiform papillae are the most numerous papillae and increase friction between the tongue and the food. The filiform papillae of the human and porcine tongues have the same shape and similar keratinisation processes and the interpapillary epithelium is parakeratotic.

Porcine tongues were stored in a freezer at approximately −20° C. In order to prepare the tongues for testing, each one was thawed, rinsed with cold tap water, patted dry with a paper towel, and two pieces were cut approximately 2.5" from the anterior of the tongue for use. Each piece of the tongue constitutes one tongue sample. Each tongue sample was placed on the aluminum platform with a plastic plate bolted on top to secure the sample. The reverse side of this platform had the exposed surface of the tongue. The aluminum platform was subsequently placed with the center of the exposed region over the tactor. The MLHD was set to ten strokes with a length of 22 mm and a normal force of 0.1 N. Each tongue sample was tested in ambient temperature and humidity.

Five mouthwash solutions listed in Table 1a were tested on 10 tongue samples each (n=10). Final concentrations were as follows: Hemp Seed Oil: 1%, Caprylyl Glycol: 0.25%, Aloe Vera Oil: 0.25%, and Hyaluronic Acid: 0.05%. The tongue samples were dried in ambient conditions for 45 minutes after which the friction coefficient was determined. Those tongue samples not treated with artificial saliva or mouthwash are referred to as untreated. Subsequent to drying the tongue samples, a coating of 0.5 mL of artificial saliva was evenly applied onto each tongue sample in order to simulate a natural condition. This was performed to simulate a general oral condition where oral tissues are always coated with some level of saliva. Next was applied a 0.5 mL coating of a selected mouthwash solution.

Tables 1a and 1b: Mouthwash Formulations

| Mouthwash Abbreviation | Key Ingredients |
| --- | --- |
| A | Glycerin, Xylitol, Sorbitol, Propylene glycol, Poloxamer 407, Hydroxymethyl cellulose |
| B | Hemp seed oil, White Mineral Oil (WMO), Glycerin, Sorbitol, Na-saccharin, Sucralose, Citric acid |
| C | Hemp Seed Oil, Caprylyl Glycol, WMO, Glycerin, Sorbitol, Na-saccharin, Sucralose, Citric Acid |
| D | Hemp seed oil, Caprylyl glycol, Aloe vera oil, WMO, Glycerin, Sorbitol, Na-saccharin, Sucralose, Citric acid |
| E | Hemp seed oil, Caprylyl Glycol, Hyaluronic Acid, WMO, Glycerin, Sorbitol, Na-saccharin, Sucralose, Citric acid |

TABLE 1b

Mouthwash Formulations

| Ingredient | Mouthwash B (Hemp Seed Oil, HSO) | Mouthwash C (HSO + Caprylyl Glycol, CG) | Mouthwash D (HSO + CG + Aloe Vera Oil, AV) | Mouthwash E (HSO + CG + Hyaluronic Acid, HA) |
|---|---|---|---|---|
| White mineral oil-Heavy | 13.0000 | 13.0000 | 13.0000 | 13.0000 |
| DPMW Peppermint type LC Flavor | 1.40000 | 1.4000 | 1.4000 | 1.4000 |
| Demineralized water | 71.3124 | 71.0624 | 70.8124 | 71.0124 |
| 99.0%-101.0% Glycerin | 7.5000 | 7.5000 | 7.5000 | 7.5000 |
| Hemp seed oil | 1.0000 | 1.0000 | 1.0000 | 1.0000 |
| Caprylyl glycol | 0.0000 | 0.2500 | 0.2500 | 0.2500 |
| Aloe Vera Oil | 0.0000 | 0.0000 | 0.2500 | 0.0000 |
| Hyaluronic Acid | 0.0000 | 0.0000 | 0.0000 | 0.0500 |
| Potassium sorbate | 0.1000 | 0.1000 | 0.1000 | 0.1000 |
| Sodium saccharin | 0.0800 | 0.0800 | 0.0800 | 0.0800 |
| Cetylpyridinium chloride | 0.0750 | 0.0750 | 0.0750 | 0.0750 |
| Sorbitol - Non-Crystal - 70% soln | 5.5000 | 5.5000 | 5.5000 | 5.5000 |
| Citric acid - anhydrous | 0.0300 | 0.0300 | 0.0300 | 0.0300 |
| Sucralose | 0.0020 | 0.0020 | 0.0020 | 0.0020 |
| FD&C Blue No. 1 (CI 42090) | 0.0006 | 0.0006 | 0.0006 | 0.0006 |

TABLE 2

Reduction in friction coefficient on porcine tongue surface treated with mouthwash products.

| | Friction Coefficient (n = 10) | |
|---|---|---|
| Mouthwash | Untreated tongue (stdev) | Treated tongue (stdev) |
| A | 0.8330 (0.1558) | 0.4656 (0.0819) |
| B | 0.7879 (0.0593) | 0.4018 (0.0400) |
| C | 0.7492 (0.0906) | 0.3902 (0.0409) |
| D | 0.6969 (0.0782) | 0.3781 (0.0398) |
| E | 0.7032 (0.0925) | 0.3631 (0.0451) |

These mouthwash solutions resulted in statistically significant differences in the friction coefficient relative to each other. Certain mouthwash formulations, e.g. mouthwash containing hemp seed oil and caprylyl glycol, produced lower friction coefficients compared to the control formulation of Mouthwash A and untreated samples. We hypothesize that lower friction coefficients here correlate with a distinct sensation of smoothness (oral comfort) while maintaining a sensation of hydration (high moisture level) for a subject.

Example 2—In Vitro Analysis of Moisture Retention Capacity

A qualitative method was developed to evaluate and demonstrate moisture retention capacity of mouthwash products. This method utilizes Vitro Skin™ (IMS Inc., Portland, ME) as a model substrate. Vitro Skin™ is an advanced testing substrate that mimics the surface properties of human skin and contains both protein and lipid components. Its topography, pH, critical surface tension and ionic strength are similar to human skin.

Briefly, 20 mm diameter Vitro Skin™ sheets were punched out and placed in a six well plastic plate. 50 μl of deionized water was then added on to the Vitro Skin™ surface followed by 100 μl of the mouthwash products. The liquid was mixed and spread over the Vitro Skin™ surface. Samples were left at room temperature over night without the lid. After 18 hours, volunteers were asked to visually inspect the samples and rate the level of moisture present on the Vitro Skin™ surface from 1 to 5, with 5 being maximum level of moisture. Inspections were performed in a blinded fashion. A total of 12 inspection volunteers participated. Total wellness score is the accumulated 12 individual ratings. For example, a total wellness score of 60 is achieved when all 12 inspection volunteers rate the samples at a level of moisture of 5. Mouthwash F comprised sorbitol, propylene glycol, poloxamer 407, sodium lauryl sulfate, flavor, Na-benzoate, Na-saccharin, phosphoric acid, and eucalyptol.

Results are summarized in Table 3. Mouthwash containing hemp seed oil and caprylyl glycol retained a superior moisture level when compared to the alternative mouthwash products. Surprisingly, all 12 panelists scored the hemp seed oil and caprylyl glycol formulation, whereas the hemp seed oil alone had an average score of 3. Based on these results, a mouthwash formula with hemp seed oil in combination with caprylyl glycol may be able to lock in moisture in the oral cavity for a longer period of time. Such moisture retainment may provide a subject effective relief from dry mouth and discomfort.

TABLE 3

Human visual scoring of moisture retention by mouthwash products (Score = 0-5, 5 being maximum moisture level).

| Mouthwash | Total Wetness Score (visual) N = 12 (stdev) | Average Wetness Score |
|---|---|---|
| A | 33 (1.22) | 2.8 |
| B | 36 (0.85) | 3 |
| C | 60 (0.0) | 5 |
| F | 34 (0.83) | 2.8 |

While the present invention has been described with reference to embodiments, it will be understood by those skilled in the art that various modifications and variations may be made therein without departing from the scope of the present invention.

The invention claimed is:

1. An oral care composition comprising:
   a. hemp seed oil at a concentration from 0.8 to 1.2%, by weight of the composition;
   b. caprylyl glycol at a concentration of 0.15 to 0.35% by weight of the composition;
   c. optionally aloe vera at a concentration of 0.15 to 0.35%, by weight of the composition;
   d. optionally hyaluronic acid at a concentration of 0.01 to 0.1%, by weight of the composition; and
   e. water or a water-alcohol mixture in the amount of at least 70% by weight;
   and wherein the composition further comprises one or more humectants selected from glycerin, and sorbitol; and optionally white mineral oil and/or a surfactant;
   wherein the composition is formulated as a mouth wash which is substantially liquid, and wherein the composition does not comprise an enzyme, an abrasive or a whitening agent.

2. The oral care composition of claim 1, wherein said composition has a moisture retention capacity of at least 4.8, as measured in an in vitro moisture retention capacity assay.

3. The oral care composition of claim 1, wherein said hemp seed oil is present at a concentration of 1.0% by weight of the composition.

4. The oral care composition of claim 1, wherein said caprylyl glycol is present at a concentration of 0.25%, by weight of the composition.

5. The oral care composition of claim 1, further comprising aloe vera at a concentration from 0.15 to 0.35% by weight of the composition.

6. The oral care composition of claim 5, wherein the aloe vera is present at a concentration of 0.25% by weight of the composition.

7. The oral composition of claim 1, further comprising hyaluronic acid at a concentration from 0.01 to 0.1% by weight of the composition.

8. The oral care composition of claim 7, wherein the hyaluronic acid is present at a concentration of 0.05%, by weight of the composition.

9. The oral care composition according to claim 1, wherein the composition further comprises ingredients selected from one or more of the following: buffering agents, humectants, surfactants, thickeners, breath fresheners, flavoring, fragrance, coloring, antibacterial agents, agents that interfere with or prevent bacterial attachment, calcium sources, phosphate sources, orally acceptable potassium salts, and anionic polymers.

10. The oral care composition according to claim 9, further comprising ingredients selected from vitamins and anti-adhesion agents.

11. The oral care composition of claim 1, wherein the composition further comprises a humectant and a surfactant.

12. The oral care composition of claim 11, wherein the humectant comprises glycerin and sorbitol.

13. The oral care composition of claim 12, wherein the composition comprises the humectant in an amount of 15% to 30% by weight of the composition.

14. The composition according to claim 1, wherein the composition is a dual-phase mouthwash composition comprising white mineral oil.

15. An oral care composition consisting essentially of:
    hemp seed oil at a concentration from 0.8 to 1.2%, by weight of the composition;
    caprylyl glycol at a concentration of 0.15 to 0.35% by weight of the composition;
    optionally aloe vera at a concentration of 0.15 to 0.35%, by weight of the composition; optionally hyaluronic acid at a concentration of 0.01 to 0.1%, by weight of the composition; water or a water-alcohol mixture in the amount of at least 70% by weight; one or more humectants selected from glycerin and sorbitol; optionally white mineral oil; optionally a surfactant; and one or more of a pH modifying agent, a flavoring agent, a sweetening agent, and a colorant; wherein the composition is formulated as a mouth wash which is substantially liquid.

16. The composition according to claim 15, wherein the composition is a dual-phase mouthwash composition comprising white mineral oil.

17. A method to improve oral health, comprising applying an effective amount of the oral composition according to claim 12, to the oral cavity.

18. The method of claim 17, wherein improving oral health may be selected from one or more of the following:
    a. reduce or inhibit formation of dental caries;
    b. reduce, repair or inhibit early enamel lesions;
    c. reduce or inhibit demineralization and promote remineralization of the teeth;
    d. reduce hypersensitivity of the teeth;
    e. reduce of inhibit gingivitis;
    f. promote healing of sores or cuts in the mouth;
    g. reduce levels of acid producing bacteria;
    h. increase relative levels of arginolytic bacteria;
    i. inhibit microbial biofilm formation in the oral cavity;
    j. raise and/or maintain plaque pH at levels of at least pH 5.5 following sugar challenge;
    k. reduce plaque accumulation;
    l. treat, relieve or reduce dry mouth;
    m. reduce tissue friction due to drying;
    n. enhance systemic health, including cardiovascular health;
    o. reduce erosion of the teeth;
    p. immunize the teeth against cariogenic bacteria and their effects;
    q. clean the teeth and oral cavity;
    r. reduce inflammation;
    s. increase anti-oxidant levels;
    t. reduce oral discomfort;
    u. increase lubrication;
    v. reduce tissue friction due to drying; and
    w. increase tissue hydration.

\* \* \* \* \*